United States Patent
Johnson

(10) Patent No.: US 10,072,288 B2
(45) Date of Patent: Sep. 11, 2018

(54) DETECTING SINGLE NUCLEOTIDE POLYMORPHISM USING OVERLAPPED PRIMER AND MELTING PROBE

(71) Applicant: Roche Molecular Systems, Inc., Pleasanton, CA (US)

(72) Inventor: Jenny A. Johnson, Castro Valley, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 229 days.

(21) Appl. No.: 14/076,979

(22) Filed: Nov. 11, 2013

(65) Prior Publication Data

US 2015/0132751 A1    May 14, 2015

(51) Int. Cl.
*C12Q 1/68* (2018.01)
*C07H 21/00* (2006.01)
*C12Q 1/6827* (2018.01)
*C12Q 1/6816* (2018.01)
*C12Q 1/6844* (2018.01)

(52) U.S. Cl.
CPC ......... *C12Q 1/6827* (2013.01); *C12Q 1/6816* (2013.01); *C12Q 1/6846* (2013.01)

(58) Field of Classification Search
CPC .................................. C12Q 1/68; C12P 19/34
See application file for complete search history.

(56) References Cited

U.S. PATENT DOCUMENTS

| | | | |
|---|---|---|---|
| 5,639,611 A * | 6/1997 | Wallace | C12Q 1/6858 435/6.11 |
| 5,723,591 A | 3/1998 | Livak et al. | |
| 7,319,022 B1 | 1/2008 | Mahoney et al. | |
| 7,723,038 B2 | 5/2010 | Mahoney et al. | |
| 8,067,177 B2 | 11/2011 | Mahoney et al. | |
| 8,323,929 B2 | 12/2012 | Wang et al. | |
| 2003/0175728 A1 * | 9/2003 | Belousov | C07C 245/08 435/6.1 |
| 2006/0281099 A1 * | 12/2006 | Breneman | C12Q 1/6818 435/6.18 |
| 2010/0267012 A1 * | 10/2010 | Bergeron | C12Q 1/14 435/6.1 |
| 2013/0059294 A1 * | 3/2013 | Ren | C12Q 1/706 435/5 |
| 2013/0122493 A1 | 5/2013 | Xu et al. | |
| 2014/0017685 A1 * | 1/2014 | Fu | C12Q 1/6827 435/6.11 |
| 2014/0170650 A1 * | 6/2014 | Froehner | C12Q 1/6858 435/6.11 |

FOREIGN PATENT DOCUMENTS

| | | | |
|---|---|---|---|
| WO | 2011146403 A2 | | 11/2011 |
| WO | 2012095629 A2 | | 7/2012 |
| WO | WO 2012/095639 | * | 7/2012 |
| WO | PCT/EP2014/074111 | | 2/2015 |

OTHER PUBLICATIONS

Darby et al., High throughput measurement of duplex, triplex and quadruplex melting curves using molecular beacons and a LightCycler. Nucleic Acids Research 30(9) : e39 (2002).*
Giesendorf et al., Molecular beacons: a new approach for semiautomated mutation analysis. Clinical Chemistry 44 (3) : 482 (1998).*
Howell et al., Dynamic allele-specific hybridization. Nature Biotechnology 17 : 87 (1999).*
Kwok, Methods for Genotyping Single Nucleotide Polymorphisms. Annual Reviews Genomics Human Genetics 2 :235 (2001).*
Prince et al.,.Robust and Accurate Single Nucleotide Polymorphism Genotyping by Dynamic Allele-Specific Hybridization (DASH): Design Criteria and Assay Validation. Genome Research 11: 152 (2001).*
The Stratagene Catalog p. 39 (1988).*
Tyagi et al. Multicolor molecular beacons for allele discrimination. Nature Biotechnology 16 : 49 (1998).*
Shumaker et al., Mutation Detection by Primer Extension. Human Mutation 7:346-354 (1996).*
Afonia et al. 32 (4) : 940 (2002).*
Ahern H., The Scientist 9(15) : 20 (1995).*
Bernard et al., Am. J. of Pathology 153 (4) :1055 (1998).*
Fu et al., PLoS One 7(1) : e30340 (Jan. 2012).*
Kwok et al., Nucleic Acids Research 18(4) :999 (1990).*
Lay et al. Clinical Chemistry 43(12) : 2262 (1997).*
Edwards and Logan, Mutation Detection by Real-Time PCR, Current PCR, Horizon Scientific Press.
Huang et al., 2011, PLoS ONE 6(4) e19206.
Luo et al., 2011, J. Clin. Microbiol., 49(9)3132-3138.

* cited by examiner

*Primary Examiner* — Ethan C Whisenant
(74) *Attorney, Agent, or Firm* — David J. Chang; M. Reza Savari

(57) ABSTRACT

Methods for the detection of the presence or absence of a single nucleotide polymorphism (SNP) in a target nucleic acid in a biological or non-biological sample are described. The methods can include performing an amplifying step using primers, a hybridizing step utilizing a melting probe, and a detecting step, wherein a decreasing shift in the predefined melting temperature of the melting probe is indicative of the presence of the SNP in the sample and wherein the absence of a decreasing shift in the predefined melting temperature of the melting probe is indicative of the absence of the SNP in the sample.

9 Claims, 5 Drawing Sheets

Specification includes a Sequence Listing.

SEQUENCE LISTING

```
<160> NUMBER OF SEQ ID NOS: 20

<210> SEQ ID NO 1
<211> LENGTH: 16
<212> TYPE: DNA
<213> ORGANISM: Artificial Sequence
<220> FEATURE:
<223> OTHER INFORMATION: Oligonucleotide

<400> SEQUENCE: 1
tgtgggtcaa ccccga                                                    16
```

```
<210> SEQ ID NO 2
<211> LENGTH: 20
<212> TYPE: DNA
<213> ORGANISM: Artificial Sequence
<220> FEATURE:
<223> OTHER INFORMATION: Oligonucleotide

<400> SEQUENCE: 2
cgcttgtggg tcaaccccga                                                   20

<210> SEQ ID NO 3
<211> LENGTH: 20
<212> TYPE: DNA
<213> ORGANISM: Artificial Sequence
<220> FEATURE:
<223> OTHER INFORMATION: Oligonucleotide

<400> SEQUENCE: 3
cgcttgtcgg tcaaccccga                                                   20

<210> SEQ ID NO 4
<211> LENGTH: 20
<212> TYPE: DNA
<213> ORGANISM: Artificial Sequence
<220> FEATURE:
<223> OTHER INFORMATION: Oligonucleotide

<400> SEQUENCE: 4
cgcttgcggg tcaaccccga                                                   20

<210> SEQ ID NO 5
<211> LENGTH: 20
<212> TYPE: DNA
<213> ORGANISM: Artificial Sequence
<220> FEATURE:
<223> OTHER INFORMATION: Oligonucleotide

<400> SEQUENCE: 5
cgcttgtagg tcaaccccga                                                   20

<210> SEQ ID NO 6
<211> LENGTH: 20
<212> TYPE: DNA
<213> ORGANISM: Artificial Sequence
<220> FEATURE:
<223> OTHER INFORMATION: Oligonucleotide

<400> SEQUENCE: 6
cgcttgaggg tcaaccccga                                                   20

<210> SEQ ID NO 7
<211> LENGTH: 20
<212> TYPE: DNA
<213> ORGANISM: Artificial Sequence
<220> FEATURE:
<223> OTHER INFORMATION: Oligonucleotide

<400> SEQUENCE: 7
cgcttgtggg tcaaccccta                                                   20

<210> SEQ ID NO 8
<211> LENGTH: 20
<212> TYPE: DNA
<213> ORGANISM: Artificial Sequence
<220> FEATURE:
<223> OTHER INFORMATION: Oligonucleotide
```

<400> SEQUENCE: 8
cgcttgtggg tcaaccccaa                                               20

<210> SEQ ID NO 9
<211> LENGTH: 20
<212> TYPE: DNA
<213> ORGANISM: Artificial Sequence
<220> FEATURE:
<223> OTHER INFORMATION: Oligonucleotide

<400> SEQUENCE: 9
cgcttgtggg tcaaccccca                                               20

<210> SEQ ID NO 10
<211> LENGTH: 19
<212> TYPE: DNA
<213> ORGANISM: Artificial Sequence
<220> FEATURE:
<223> OTHER INFORMATION: Oligonucleotide

<400> SEQUENCE: 10
gcgcttgtgg gtcaacccc                                                19

<210> SEQ ID NO 11
<211> LENGTH: 19
<212> TYPE: DNA
<213> ORGANISM: Artificial Sequence
<220> FEATURE:
<223> OTHER INFORMATION: Oligonucleotide

<400> SEQUENCE: 11
cgcttgtggg tcaacccccg                                               19

<210> SEQ ID NO 12
<211> LENGTH: 19
<212> TYPE: DNA
<213> ORGANISM: Artificial Sequence
<220> FEATURE:
<223> OTHER INFORMATION: Oligonucleotide

<400> SEQUENCE: 12
cgcttgtggg tcaacccccg                                               19

<210> SEQ ID NO 13
<211> LENGTH: 19
<212> TYPE: DNA
<213> ORGANISM: Artificial Sequence
<220> FEATURE:
<223> OTHER INFORMATION: Oligonucleotide

<400> SEQUENCE: 13
cgcttgtcgg tcaacccccg                                               19

<210> SEQ ID NO 14
<211> LENGTH: 19
<212> TYPE: DNA
<213> ORGANISM: Artificial Sequence
<220> FEATURE:
<223> OTHER INFORMATION: Oligonucleotide

<400> SEQUENCE: 14
cgcttgcggg tcaacccccg                                               19

<210> SEQ ID NO 15

```
<211> LENGTH: 19
<212> TYPE: DNA
<213> ORGANISM: Artificial Sequence
<220> FEATURE:
<223> OTHER INFORMATION: Oligonucleotide

<400> SEQUENCE: 15
cgcttgtagg tcaaccccg                                           19

<210> SEQ ID NO 16
<211> LENGTH: 19
<212> TYPE: DNA
<213> ORGANISM: Artificial Sequence
<220> FEATURE:
<223> OTHER INFORMATION: Oligonucleotide

<400> SEQUENCE: 16
cgcttgaggg tcaaccccg                                           19

<210> SEQ ID NO 17
<211> LENGTH: 19
<212> TYPE: DNA
<213> ORGANISM: Artificial Sequence
<220> FEATURE:
<223> OTHER INFORMATION: Oligonucleotide

<400> SEQUENCE: 17
cgcttgtggg tcaacccct                                           19

<210> SEQ ID NO 18
<211> LENGTH: 19
<212> TYPE: DNA
<213> ORGANISM: Artificial Sequence
<220> FEATURE:
<223> OTHER INFORMATION: Oligonucleotide

<400> SEQUENCE: 18
cgcttgtggg tcaaccca                                            19

<210> SEQ ID NO 19
<211> LENGTH: 19
<212> TYPE: DNA
<213> ORGANISM: Artificial Sequence
<220> FEATURE:
<223> OTHER INFORMATION: Oligonucleotide

<400> SEQUENCE: 19
cgcttgtggg tcaaccccc                                           19

<210> SEQ ID NO 20
<211> LENGTH: 19
<212> TYPE: DNA
<213> ORGANISM: Artificial Sequence
<220> FEATURE:
<223> OTHER INFORMATION: Oligonucleotide

<400> SEQUENCE: 20
cgcttgtggg tcaacccct                                           19
```

DETECTING SINGLE NUCLEOTIDE POLYMORPHISM USING OVERLAPPED PRIMER AND MELTING PROBE

FIELD OF THE INVENTION

The present invention relates to the field of polymerase chain reaction (PCR) based diagnostic, and more particularly, to methods for amplifying and detecting sequence variations in target nucleic acids having single nucleotide polymorphism (SNP).

BACKGROUND OF THE INVENTION

Detection of SNPs by PCR using fluorescently labeled melting probes has been previously described (see, e.g., Huang et al., 2011, PLoS ONE 6(4) e19206 and Luo et al., 2011, J. Clin. Microbiol., 49(9)3132-3138). Traditional melting works by analyzing the post-PCR melting temperature of a fluorescently labeled probe with target in the absence of a SNP and in the presence of a SNP. A well-designed melting probe yields a melting temperature ($T_m$) which is highest in the absence of a SNP, and any base pair changes that occur in the probe binding region causes a shift (decrease) in melting temperature. The shift in melting temperature can be used to distinguish of wild type (WT) and mutant (MT) targets.

Unfortunately, some SNPs of interest are located in non-conserved gene regions where near-by sequence heterogeneity causes an unwanted shift in probe melting temperature. This makes it difficult to distinguish WT sequences with silent mutations from the relevant SNPs of interest. SNPs associated with micro-organism drug resistance are some examples where specific SNPs conferring drug resistance are located in gene regions that contain near-by WT silent mutations. In such a case, any silent mutation(s) in the probe binding region near the SNP of interest could also generate a shift in probe melting temperature and yield a false-positive result. Thus, there is a need for more accurate and effective way to detect only the SNP of interest in a target nucleic acid. Embodiments of the present invention can solve the existing problems of sequence heterogeneity and enable a well-designed melting probe to detect only the SNP of interest without interference from nearby silent mutations.

SUMMARY OF THE INVENTION

Embodiments of the present invention relates to methods and kits for the rapid detection of the presence or absence of a SNP in a target nucleic acid in a biological or non-biological sample, for example, detection of one or more SNPs by real-time polymerase chain reaction in a single test tube.

In one embodiment, a method for detecting a SNP in a target nucleic acid in a sample is provided. The method for detecting a SNP includes the steps of performing an amplifying step which includes contacting the sample with a primer having a first wild type nucleic acid sequence to produce an amplification product if any target nucleic acid is present in the sample; performing a hybridizing step which includes contacting the amplification product with a melting probe having a second wild type nucleic acid sequence having a predefined melting temperature, wherein the second wild type nucleic acid sequence of the melting probe overlaps with the first wild type nucleic acid sequence of the primer and extends out at one end by one or more nucleotides over an area of the target nucleic acid where the SNP is located; and detecting the presence or absence of the SNP in the amplification product, wherein a decreasing shift in the predefined melting temperature of the melting probe is indicative of the presence of the SNP in the sample and wherein the absence of a decreasing shift in the predefined melting temperature of the melting probe is indicative of the absence of the SNP in the sample.

In another embodiment, an alternative method for detecting a SNP in a target nucleic acid in a sample is provided. The alternative method for detecting SNP includes the steps of performing an amplifying step which includes contacting the sample with a primer having a wild type nucleic acid sequence to produce an amplification product if any target nucleic acid is present in the sample; performing a hybridizing step which includes contacting the amplification product with a melting probe having a SNP specific nucleic acid sequence having a predefined melting temperature, wherein the SNP specific nucleic acid sequence of the melting probe overlaps with the wild type nucleic acid sequence of the primer and extends out at one end by one or more nucleotides over an area of the target nucleic acid where the SNP is located; and detecting the presence or absence of the SNP in the amplification product; wherein a decreasing shift in the predefined melting temperature of the melting probe is indicative of the absence of the SNP in the sample and wherein the absence of a decreasing shift in the predefined melting temperature of the melting probe is indicative of the presence of the SNP in the sample.

In yet another embodiment, a primer and probe set for detecting a SNP in a target nucleic acid in a sample is provide. The primer and probes set can be included in a kit that can be provided for detecting the SNP. The kit can include a primer having a first wild type nucleic acid sequence to produce an amplification product if any target nucleic acid is present in the sample; and a melting probe having a second wild type nucleic acid sequence having a predefined melting temperature, wherein the second wild type nucleic acid sequence of the melting probe overlaps the first wild type nucleic acid sequence of the primer and extends out at one end by one or more nucleotides over an area of the target nucleic acid where the SNP is located; wherein the presence or absence of the SNP in the amplification product is detected whereby a decreasing shift in the predefined melting temperature of the melting probe is indicative of the presence of the SNP in the sample and whereby the absence of a decreasing shift in the predefined melting temperature of the melting probe is indicative of the absence of the SNP in the sample.

In another embodiment, an alternative primer and probe set for detecting a SNP in a target nucleic acid in a sample is provide. The alternative primer and probes set can be included in a kit that can be provided for detecting the SNP. The kit can include a primer having a wild type nucleic acid sequence to produce an amplification product if any target nucleic acid is present in the sample; and a melting probe having a SNP specific nucleic acid sequence having a predefined melting temperature, wherein the SNP specific nucleic acid sequence of the melting probe overlaps the first wild type nucleic acid sequence of the primer and extends out at one end by one or more nucleotides over an area of the target nucleic acid where the SNP is located; wherein the presence or absence of the SNP in the amplification product is detected whereby a decreasing shift in the predefined melting temperature of the melting probe is indicative of the absence of the SNP in the sample and wherein the absence of a decreasing shift in the predefined melting temperature of the melting probe is indicative of the presence of the SNP in the sample.

In some embodiments, the kit can include probes already labeled with donor and corresponding acceptor fluorescent moieties, or can include fluorophoric moieties for labeling the probes. The kit can also include nucleoside triphosphates, nucleic acid polymerase, and buffers necessary for the function of the nucleic acid polymerase. The kit can also include a package insert and instructions for using the primers, probes, and fluorophoric moieties to detect the presence or absence of the SNP in a sample.

In certain of these embodiments, the oligonucleotides (primers and/or probes) have 40 or fewer nucleotides (e.g., 25 or fewer nucleotides, 20 or fewer nucleotides, etc.) In some embodiments, the oligonucleotides comprise at least one modified nucleotide, e.g., to alter nucleic acid hybridization stability relative to unmodified nucleotides.

In some embodiments, the melting probes may include a nucleic acid sequence that permits secondary structure formation. The melting probe can be labeled with a fluorescent moiety at the 5' terminus, and a corresponding acceptor moiety at the 3' terminus to quench the fluorescence of unbound melting probes. The nucleic acid sequence of the melting probes can provide randomly coiled conformation which enables fluorescence quenching unless the probe is hybridized to its target. Such secondary structure formation generally results in spatial proximity between the first (e.g., flurophore) and second (e.g., quencher) fluorescent moieties. For example, the non-hybridized melting probe may quenched or only be weakly fluorescent, but the melting probe may become more strongly fluorescent when hybridized with its target. After denaturation from its target, the melting probe can return back to its quenched or weakly fluorescent state. Accordingly, the fluorescence intensity of the melting probe-target complex decreases as temperature increases in a target-dependent manner, yielding different melting temperature value for each target derived from the melting peak.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In addition, the materials, methods, and examples are illustrative only and not intended to be limiting. All publications, patent applications, patents, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the drawings and detailed description, and from the claims.

DETAILED DESCRIPTION OF THE INVENTION

Detection of one or more SNPs in target nucleic acid in a sample by nucleic acid amplification provides a rapid and accurate method of detection for the SNPs. A real-time assay for detecting an SNP in target nucleic acid in a sample is described herein, as are primers and probes sets for detecting the SNPs. The increased sensitivity of real-time PCR for detection of SNPs compared to other methods, as well as the improved features of real-time PCR including sample containment and real-time detection of the amplified product, make feasible the implementation of this technology for routine diagnosis and SNP detection in the clinical laboratory.

Figure 1:
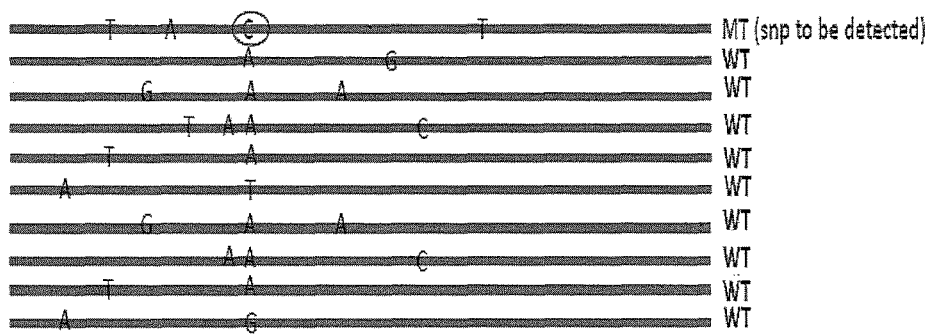
FIG. 1 shows a schematic view of an exemplary SNP to be detected amongst a diverse WT population with the SNP being located in non-conserved gene regions having nearby sequence heterogeneity.
Figure 2:
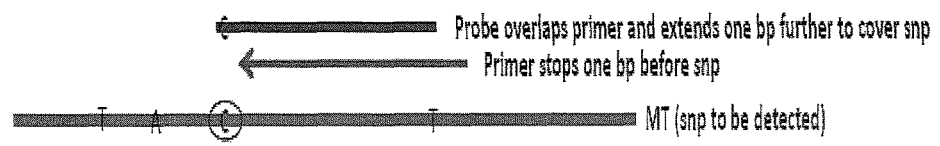
FIG. 2 shows a schematic view of an exemplary primer and probe design for detection of a SNP, with a primer sequence that will "prime" the PCR to begin one base pair before the SNP to be detected, and an overlapping melting probe with same sequence as the primer and extends one base pair longer, covering the SNP location.
Figure 3:
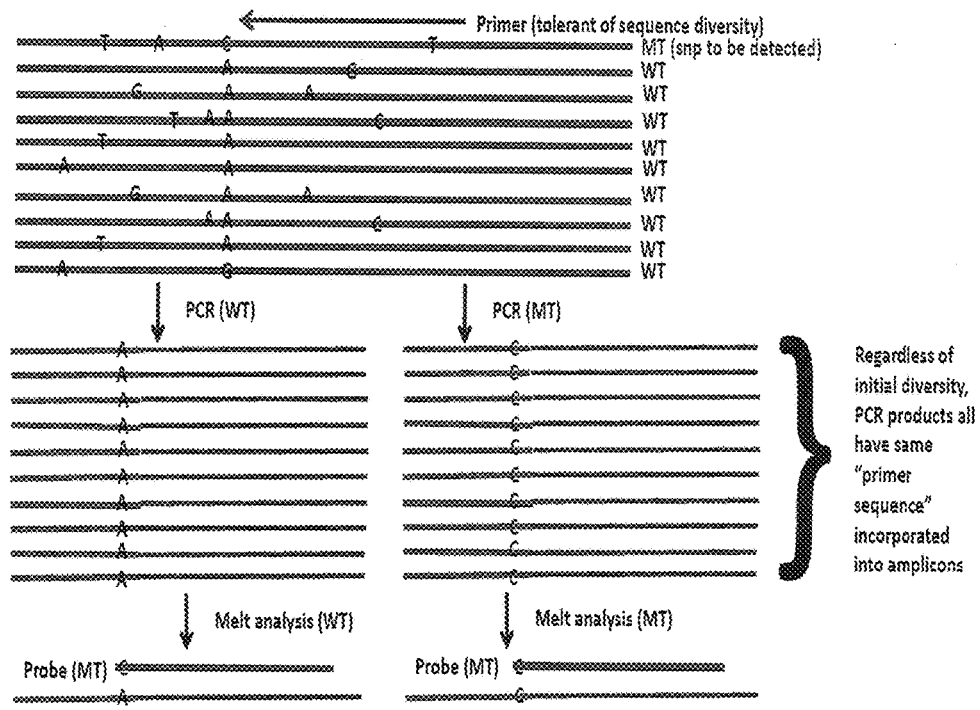
FIG. 3 shows a schematic view of an exemplary PCR reaction utilizing the overlapping primer and probe design for detection of a SNP.
Figure 4:
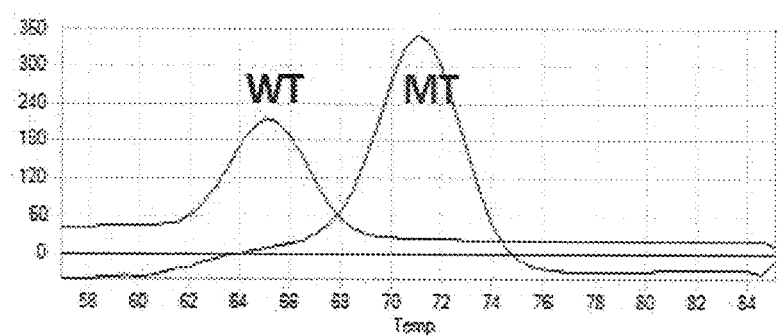
FIG. 4 shows a schematic view of an exemplary melt curve analysis of the PCR reaction products utilizing the overlapping primer and probe design for detection of a SNP.

Embodiments of the present invention allow the detection of one specific SNP, e.g., amongst a diverse WT population (FIG. 1). Embodiments include methods of detection of a SNP utilizing an overlapping primer and probe design (also referred to as stacked primer and probe), wherein the sequence of a primer and a melting probe overlap one another in order to detect the SNP of interest that lies in a non-conserved gene region and contains nearby silent mutations. A primer sequence (forward or reverse) can be designed that will 'prime' the PCR to begin one or more base pairs before the SNP to be detected, and an overlapping melting probe can be designed with the same sequence as the primer but extends one or more base pairs longer than the primer to extend over and cover the SNP location of the target nucleic acid (FIG. 2). The primer can be designed to be tolerant and robust enough to 'prime' the PCR reaction regardless of sequence diversity under the primer region on the target nucleic acid. Appropriate primer design may include modified bases (stabilizers) that improve the binding capacity of the primer in the presence of mismatches (sequence diversity). This way, regardless of the initial diversity of the target nucleic acid in the area where the primer hybridizes, the PCR amplification products will all have same primer sequence incorporated into the generated amplicons (FIG. 3). Melting analysis of the PCR products with the overlapping primer and probe allows for detecting the presence or absence of the SNP in the amplification product, wherein a decreasing shift in the predefined melting temperature of the melting probe is indicative of the presence of the SNP in the sample (FIG. 4).

The methods may include performing at least one cycling step that includes amplifying one or more portions of a target nucleic acid molecule, e.g., a gene target containing the SNP of interest to be detected, in a sample using one or more primers or one or more pairs of primers. The terms "primer", "primers", and "primer pairs" as used herein refer to oligonucleotide primer(s) that specifically anneal to a region of the target nucleic acid sequence, and initiate synthesis therefrom under appropriate conditions. Each of the discussed primers can be designed to anneal to a target nucleic acid and adjacent to the SNP of interest to be detected in the target nucleic acid molecule, such that at least a portion of each amplification product contains the nucleic acid sequence corresponding to the respective targets and SNP, if present. The primer can be designed to anneal adjacent the SNP of interest, e.g., next to, nearby, slightly upstream, or slightly downstream, by, e.g., one, two, three, or more nucleotides. Thus, contacting the sample with a primer having a first wild type nucleic acid sequence can produce an amplification product if any target nucleic acid is present in the sample, whether or not the SNP of interest is present in the target nucleic acid molecule.

The method can also include a hybridizing step that includes contacting the amplification product with a melting probe having a second wild type nucleic acid sequence, wherein the sequence of the second wild type nucleic acid sequence of the melting probe overlaps (is the same as) the first wild type nucleic acid sequence of the primer, and extends out at one end by one or more nucleotides over an area of the target nucleic acid where the SNP is located. Depending on a chosen design for an assay, the melting probe can comprise one or more predefined melting temperature profiles, including, e.g., a first predefined temperature at which the melting probe melts, or unhybridizes, from a perfectly matched wild type nucleic acid target. Thus, an observation a decreasing shift in the predefined melting temperature of the melting probe can indicate a mismatch in the sequence of the wild type melting probe and the nucleic acid target, i.e., the presence of a SNP in the target nucleic acid in the sample. This is because a mismatch in the sequence of the wild type melting probe and the presence of the SNP in the target results in a lower melting temperature of the melting probe when compared to a completely matched melting probe and wild type target sequence without the SNP. The melting temperature profiles of the melting probe can also include, e.g., a second predefined melting temperature at which the melting probe having a wild type sequence melts from a known SNP in a nucleic acid target, such that when the second predefined melting temperature is observed, not only the presence of an SNP is determined, but also the identity of the SNP can be distinguished from the various possibilities of the SNPs for the nucleic acid target. In this way, for a particular target, a plurality of predefined melting temperatures depending on the identity of various possible SNP nucleotide variations can be predetermined or standardized, which distinguish between the SNP nucleotide variations (see, e.g., FIG. 6). The melting temperature can be established by experimentation for each particular base pair change (dA, dT, dC, or dG) in a single location under the probe region.

Alternatively, the melting probe can comprise a SNP specific sequence for a known SNP to be detected. In such a case, one predefined melting temperature profiles may include a first predefined temperature at which the SNP specific melting probe melts from a perfectly matched SNP containing nucleic acid target, and thus an observation of a the predefined melting temperature can indicate the presence of the specific SNP in the target nucleic acid sequence because a perfectly matched SNP specific melting probe with the SNP containing target nucleic acid sequence will not result in a decreasing shift in the melting temperature. Furthermore, in such a case a decreasing shift in the predefined melting temperature of the SNP specific melting probe can indicate a mismatch in the sequence of the SNP specific melting probe and the nucleic acid target, e.g., the absence of the SNP and the presence of the wild type nucleic acid, or the presence of a different SNP, in the sample. If a target nucleic acid molecule is known to have a plurality of SNPs that are of interest for detection, a plurality of melting probes can be designed as explained above, each having a wild type sequence or a SNP specific sequence for the detection and characterization of the multiple SNPs of interest.

The presence of the amplification product is indicative of the presence of the target nucleic acid in the sample. The presence or absence of a decreasing shift in the predefined melting temperature of the melting probe is indicative of the presence or absence of the SNP in the target nucleic acid target in the sample. Depending on whether or not the target nucleic acid contains the SNP of interest to be detected, the produced amplification product according the present methods will contain the target nucleic acid sequence that are complementary to the detectable melting probes which can be design to either contain the wild type sequence or the SNP specific sequence depending the assay design as described above. Each cycling step includes an amplification step, a hybridization step, and a detection step, in which the sample is contacted with the one or more detectable melting probes for detection of the presence or absence of the SNP of interest in the target nucleic acid sequence in the sample.

Embodiments of the SNP detection methods are capable to detect and discriminate between the wild type target nucleic acid and the SNP containing target nucleic acid in a single PCR tube. The methods described here can be designed to simultaneously detect both the wild type and the SNP containing target nucleic acid sequences, and discriminate them in a single PCR reaction.

As used herein, the term "amplifying" refers to the process of synthesizing nucleic acid molecules that are complementary to one or both strands of a template nucleic acid molecule (e.g., target nucleic acid molecules for Human immunodeficiency virus (HIV) or *Mycobacterium tuberculosis* (MTB), or Hepatitis C virus (HCV)). Amplifying a nucleic acid molecule typically includes denaturing the template nucleic acid, annealing primers to the template nucleic acid at a temperature that is below the melting temperatures of the primers, and enzymatically elongating from the primers to generate an amplification product. Amplification typically requires the presence of deoxyribonucleoside triphosphates, a DNA polymerase enzyme (e.g., Platinum® Taq) and an appropriate buffer and/or co-factors for optimal activity of the polymerase enzyme (e.g., $MgCl_2$ and/or KCl).

The term "primer" is used herein as known to those skilled in the art and refers to oligomeric compounds, primarily to oligonucleotides but also to modified oligonucleotides that are able to "prime" DNA synthesis by a template-dependent DNA polymerase, i.e., the 3'-end of the, e.g., oligonucleotide provides a free 3'-OH group whereto further "nucleotides" may be attached by a template-dependent DNA polymerase establishing 3' to 5' phosphodiester linkage whereby deoxynucleoside triphosphates are used and whereby pyrophosphate is released. In general, primers are designed based on known template sequences. One primer primes the sense strand, and the other primes the complementary strand of the target DNA or cDNA. PCR can be performed on a uniform target DNA or RNA (i.e., targets with the same sequence) or on mixed target DNAs or RNAs, (i.e., targets with different intervening sequences flanked by conserved sequences). For mixed DNAs/RNAs (e.g., containing sequence heterogeneity) even mismatched primers can function in the PCR reaction if the sequences of the targets have enough complementarity to the mismatched primers (i.e., tolerant primers).

The term "hybridizing" refers to the annealing of one or more probes to an amplification product. Hybridization conditions typically include a temperature that is below the melting temperature of the probes but that avoids non-specific hybridization of the probes.

The term "thermostable polymerase" refers to a polymerase enzyme that is heat stable, i.e., the enzyme catalyzes the formation of primer extension products complementary to a template and does not irreversibly denature when subjected to the elevated temperatures for the time necessary to effect denaturation of double-stranded template nucleic acids. Generally, the synthesis is initiated at the 3' end of each primer and proceeds in the 5' to 3' direction along the template strand. Thermostable polymerases have been isolated from *Thermus fiavus, T. ruber, T. thermophilus, T. aquaticus, T. lacteus, T. rubens, Bacillus stearothermophilus*, and *Methanothermus fervidus*. Nonetheless, polymerases that are not thermostable also can be employed in PCR assays provided the enzyme is replenished.

The term "complement thereof" refers to nucleic acid that is both the same length as, and exactly complementary to, a given nucleic acid.

The term "extension" or "elongation" when used with respect to nucleic acids refers to when additional nucleotides (or other analogous molecules) are incorporated into the nucleic acids. For example, a nucleic acid is optionally extended by a nucleotide incorporating biocatalyst, such as a polymerase that typically adds nucleotides at the 3' terminal end of a nucleic acid.

The terms "identical" or percent "identity" in the context of two or more nucleic acid sequences, refer to two or more sequences or subsequences that are the same or have a specified percentage of nucleotides that are the same, when compared and aligned for maximum correspondence, e.g., as measured using one of the sequence comparison algorithms available to persons of skill or by visual inspection. Exemplary algorithms that are suitable for determining percent sequence identity and sequence similarity are the BLAST programs, which are described in, e.g., Altschul et al. (1990) "Basic local alignment search tool" *J. Mol. Biol.* 215:403-410, Gish et al. (1993) "Identification of protein coding regions by database similarity search" *Nature Genet.* 3:266-272, Madden et al. (1996) "Applications of network BLAST server" *Meth. Enzymol.* 266:131-141, Altschul et al. (1997) "Gapped BLAST and PSI-BLAST: a new generation of protein database search programs" *Nucleic Acids Res.* 25:3389-3402, and Zhang et al. (1997) "PowerBLAST: A new network BLAST application for interactive or automated sequence analysis and annotation" *Genome Res.* 7:649-656, which are each incorporated herein by reference.

A "modified nucleotide" in the context of an oligonucleotide refers to an alteration in which at least one nucleotide of the oligonucleotide sequence is replaced by a different nucleotide that provides a desired property to the oligonucleotide. Exemplary modified nucleotides that can be substituted in the oligonucleotides described herein include, e.g., a C5-methyl-dC, a C5-ethyl-dC, a C5-methyl-dU, a C5-ethyl-dU, a 2,6-diaminopurine, a C5-propynyl-dC, a C5-propynyl-dU, a C7-propynyl-dA, a C7-propynyl-dG, a C5-propargylamino-dC, a C5-propargylamino-dU, a C7-propargylamino-dA, a C7-propargylamino-dG, a 7-deaza-2-deoxyxanthosine, a pyrazolopyrimidine analog, a pseudo-dU, a nitro pyrrole, a nitro indole, 2'-0-methyl Ribo-U, 2'-0-methyl Ribo-C, an N4-ethyl-dC, an N6-methyl-dA, and the like. Many other modified nucleotides that can be substituted in the oligonucleotides of the invention are referred to herein or are otherwise known in the art. In certain embodiments, modified nucleotide substitutions modify melting temperatures (Tm) of the oligonucleotides relative to the melting temperatures of corresponding unmodified oligonucleotides. To further illustrate, certain modified nucleotide substitutions can reduce non-specific nucleic acid amplification (e.g., minimize primer dimer formation or the like), increase the yield of an intended target amplicon, and/or the like in some embodiments of the invention. Examples of these types of nucleic acid modifications are described in, e.g., U.S. Pat. No. 6,001,611, which is incorporated herein by reference.

Target Nucleic Acids and Oligonucleotides

The present description provides methods to detect SNP in a target nucleic acid by amplifying, for example, a portion of the target nucleic acid sequences, which may be any target nucleic acid sequence the in known or suspected to comprise one or more SNPs, for example target nucleic acid sequences from, e.g., HIV, HCV, or MTB that is rifampicin resistant.

For detection of SNP in the target nucleic acid sequence, primers and probes to amplify the target nucleic acid sequences can be prepared. Also, functional variants can be evaluated for specificity and/or sensitivity by those of skill in the art using routine methods. Representative functional variants can include, e.g., one or more deletions, insertions, and/or substitutions in the primers and/or probes disclosed herein. For example, a substantially identical variant of the primers or probes can be provided in which the variant has at least, e.g., 80%, 90%, or 95% sequence identity to one original primers and probes, or a complement thereof.

A functionally active variant of any of primer and/or probe may be identified which provides a similar or higher specificity and sensitivity in the presently described method or kit as compared to the respective original sequences.

As detailed above, a primer (and/or probe) may be chemically modified, i.e., a primer and/or probe may comprise a modified nucleotide or a non-nucleotide compound. A probe (or a primer) is then a modified oligonucleotide. "Modified nucleotides" (or "nucleotide analogs") differ from a natural "nucleotide" by some modification but still consist of a base or base-like compound, a pentofuranosyl sugar or a pentofuranosyl sugar-like compound, a phosphate portion or phosphate-like portion, or combinations thereof. For example, a "label" may be attached to the base portion of a "nucleotide" whereby a "modified nucleotide" is obtained. A natural base in a "nucleotide" may also be replaced by, e.g., a 7-desazapurine whereby a "modified nucleotide" is obtained as well. The terms "modified nucleotide" or "nucleotide analog" are used interchangeably in the present application. A "modified nucleoside" (or "nucleoside analog") differs from a natural nucleoside by some modification in the manner as outlined above for a "modified nucleotide" (or a "nucleotide analog").

Oligonucleotides including modified oligonucleotides and oligonucleotide analogs that amplify the target nucleic acid sequences can be designed using, for example, a computer program such as OLIGO (Molecular Biology Insights Inc., Cascade, Colo.). Important features when designing oligonucleotides to be used as amplification primers include, but are not limited to, an appropriate size amplification product to facilitate detection (e.g., by electrophoresis), similar melting temperatures for the members of a pair of primers, and the length of each primer (i.e., the primers need to be long enough to anneal with sequence-specificity and to initiate synthesis but not so long that fidelity is reduced during oligonucleotide synthesis). Typically, oligonucleotide primers are 8 to 50 nucleotides in length (e.g., 8, 10, 12, 14, 16, 18, 20, 22, 24, 26, 28, 30, 32, 34, 36, 38, 40, 42, 44, 46, 48, or 50 nucleotides in length).

In addition to a set of primers, the present methods may use one or more probes in order to detect the presence or absence of SNP in a target nucleic acid sequence. The term "probe" refers to synthetically or biologically produced nucleic acids (DNA or RNA), which by design or selection, contain specific nucleotide sequences that allow them to hybridize under defined predetermined stringencies specifically (i.e., preferentially) to "target nucleic acids". A "probe" can be referred to as a "detection probe" meaning that it detects the target nucleic acid.

In some embodiments of the present invention; the described probes can be labeled with at least one fluorescent label. In one embodiment probes can be labeled with a donor fluorescent moiety, e.g., a fluorescent dye, and a corresponding acceptor fluorescent moiety, e.g., a quencher.

Designing oligonucleotides to be used as hybridization probes can be performed in a manner similar to the design of primers. Embodiments of the present invention may use a single probe or a pair of probes for detection of the amplification product. Depending on the embodiment, the probe(s) use may comprise at least one label and/or at least one quencher moiety. As with the primers, the probes usually have similar melting temperatures, and the length of each probe must be sufficient for sequence-specific hybridization to occur but not so long that fidelity is reduced during synthesis. Oligonucleotide probes are generally 15 to 30 (e.g., 16, 18, 20, 21, 22, 23, 24, or 25) nucleotides in length.

Constructs can include vectors each containing one of a primer or a probe nucleic acid molecule. Constructs can be used, for example, as control template nucleic acid molecules. Vectors suitable for use in the present invention are commercially available and/or produced by recombinant nucleic acid technology methods routine in the art.

Constructs suitable for use in the described methods typically include, in addition to the primer and probe nucleic acid molecules, sequences encoding a selectable marker (e.g., an antibiotic resistance gene) for selecting desired constructs and/or transformants, and an origin of replication. The choice of vector systems usually depends upon several factors, including, but not limited to, the choice of host cells, replication efficiency, selectability, inducibility, and the ease of recovery.

Constructs containing primer and probe nucleic acid molecules can be propagated in a host cell. As used herein, the term host cell is meant to include prokaryotes and eukaryotes such as yeast, plant and animal cells. Prokaryotic hosts may include *E. coli, Salmonella typhimurium, Serratia marcescens*, and *Bacillus subtilis*. Eukaryotic hosts include yeasts such as *S. cerevisiae, S. pombe, Pichia pastoris*, mammalian cells such as COS cells or Chinese hamster ovary (CHO) cells, insect cells, and plant cells such as *Arabidopsis thaliana* and *Nicotiana tabacum*. A construct can be introduced into a host cell using any of the techniques commonly known to those of ordinary skill in the art. For example, calcium phosphate precipitation, electroporation, heat shock, lipofection, microinjection, and viral-mediated nucleic acid transfer are common methods for introducing nucleic acids into host cells. In addition, naked DNA can be delivered directly to cells (see, e.g., U.S. Pat. Nos. 5,580,859 and 5,589,466).

Polymerase Chain Reaction (PCR)

U.S. Pat. Nos. 4,683,202, 4,683,195, 4,800,159, and 4,965,188 disclose conventional PCR techniques. PCR typically employs two oligonucleotide primers that bind to a selected nucleic acid template (e.g., DNA or RNA). Primers useful in the described embodiments include oligonucleotides capable of acting as a point of initiation of nucleic acid synthesis within the target nucleic acid sequences. A primer can be purified from a restriction digest by conventional methods, or it can be produced synthetically. The primer is preferably single-stranded for maximum efficiency in amplification, but the primer can be double-stranded. Double-stranded primers are first denatured, i.e., treated to separate the strands. One method of denaturing double stranded nucleic acids is by heating.

If the template nucleic acid is double-stranded, it is necessary to separate the two strands before it can be used as a template in PCR. Strand separation can be accomplished by any suitable denaturing method including physical, chemical or enzymatic means. One method of separating the nucleic acid strands involves heating the nucleic acid until it is predominately denatured (e.g., greater than 50%, 60%, 70%, 80%, 90% or 95% denatured). The heating conditions necessary for denaturing template nucleic acid will depend, e.g., on the buffer salt concentration and the length and nucleotide composition of the nucleic acids being denatured, but typically range from about 90° C. to about 105° C. for a time depending on features of the reaction such as temperature and the nucleic acid length. Denaturation is typically performed for about 30 sec to 4 min (e.g., 1 min to 2 min 30 sec, or 1.5 min).

If the double-stranded template nucleic acid is denatured by heat, the reaction mixture is allowed to cool to a temperature that promotes annealing of each primer to its target sequence on the described target nucleic acid molecules, e.g., containing the SNP. The temperature for annealing is usually from about 35° C. to about 65° C. (e.g., about 40° C. to about 60° C.; about 45° C. to about 50° C.). Annealing times can be from about 10 sec to about 1 min (e.g., about 20 sec to about 50 sec; about 30 sec to about 40 sec). The reaction mixture is then adjusted to a temperature at which the activity of the polymerase is promoted or optimized, i.e., a temperature sufficient for extension to occur from the annealed primer to generate products complementary to the template nucleic acid. The temperature should be sufficient to synthesize an extension product from each primer that is annealed to a nucleic acid template, but should not be so high as to denature an extension product from its complementary template (e.g., the temperature for extension generally ranges from about 40° C. to about 80° C. (e.g., about 50° C. to about 70° C.; about 60° C.). Extension times can be from about 10 sec to about 5 min (e.g., about 30 sec to about 4 min; about 1 min to about 3 min; about 1 min 30 sec to about 2 min).

PCR assays can employ primer and probe nucleic acid such as RNA or DNA (cDNA). The template nucleic acid need not be purified; it may be a minor fraction of a complex mixture, such as a SNP containing nucleic acid contained in human cells. SNP containing nucleic acid molecules may be extracted from a biological sample by routine techniques such as those described in *Diagnostic Molecular Microbiology: Principles and Applications* (Persing et al. (eds), 1993, American Society for Microbiology, Washington D.C.). Nucleic acids can be obtained from any number of sources, such as plasmids, or natural sources including bacteria, yeast, viruses, organelles, or higher organisms such as plants or animals.

The oligonucleotide primers are combined with PCR reagents under reaction conditions that induce primer extension. For example, chain extension reactions generally include 50 mM KCl, 10 mM Tris-HCl (pH 8.3), 15 mM $MgCl_2$, 0.001% (w/v) gelatin, 0.5-1.0 µg denatured template DNA, 50 pmoles of each oligonucleotide primer, 2.5 U of Taq polymerase, and 10% DMSO). The reactions usually contain 150 to 320 µM each of dATP, dCTP, dTTP, dGTP, or one or more analogs thereof.

The newly synthesized strands form a double-stranded molecule that can be used in the succeeding steps of the reaction. The steps of strand separation, annealing, and elongation can be repeated as often as needed to produce the desired quantity of amplification products corresponding to the target nucleic acid molecules. The limiting factors in the reaction are the amounts of primers, thermostable enzyme, and nucleoside triphosphates present in the reaction. The cycling steps (i.e., denaturation, annealing, and extension) are preferably repeated at least once. For use in detection, the number of cycling steps will depend, e.g., on the nature of the sample. If the sample is a complex mixture of nucleic acids, more cycling steps will be required to amplify the target sequence sufficient for detection. Generally, the cycling steps are repeated at least about 20 times, but may be repeated as many as 40, 60, or even 100 times.

Fluorescence Resonance Energy Transfer (FRET)

FRET technology (see, for example, U.S. Pat. Nos. 4,996,143, 5,565,322, 5,849,489, and 6,162,603) is based on a concept that when a donor fluorescent moiety and a corresponding acceptor fluorescent moiety are positioned within a certain distance of each other, energy transfer takes place between the two fluorescent moieties that can be visualized or otherwise detected and/or quantitated. The donor typically transfers the energy to the acceptor when the donor is excited by light radiation with a suitable wavelength. The acceptor typically re-emits the transferred energy in the form of light radiation with a different wavelength.

In one example, an oligonucleotide melting probe can contain a donor fluorescent moiety and a corresponding quencher, which dissipates the transferred energy in a form other than light. When the melting probe is intact and not hybridized to its target, energy transfer typically occurs between the two fluorescent moieties such that fluorescent emission from the donor fluorescent moiety is quenched. When the melting probe hybridizes to its target nucleic acid sequence, the fluorescent moiety and a corresponding quencher become specially more separated and the melting probe becomes more strongly fluorescent. Commonly used donor-acceptor pairs include the FAM-TAMRA pair. Commonly used quenchers are DABCYL and TAMRA. Commonly used dark quenchers include BlackHole Quenchers™ (BHQ), (Biosearch Technologies, Inc., Novato, Calif.), Iowa Black™, (Integrated DNA Tech., Inc., Coralville, Iowa), BlackBerry™ Quencher 650 (BBQ-650), (Berry & Assoc., Dexter, Mich.).

Fluorescent analysis can be carried out using, for example, a photon counting epifluorescent microscope system (containing the appropriate dichroic mirror and filters for monitoring fluorescent emission at the particular range), a photon counting photomultiplier system, or a fluorometer. Excitation to initiate energy transfer can be carried out with an argon ion laser, a high intensity mercury (Hg) arc lamp, a fiber optic light source, or other high intensity light source appropriately filtered for excitation in the desired range.

As used herein with respect to donor and corresponding acceptor fluorescent moieties "corresponding" refers to an acceptor fluorescent moiety having an emission spectrum that overlaps the excitation spectrum of the donor fluorescent moiety. The wavelength maximum of the emission spectrum of the acceptor fluorescent moiety should be at least 100 nm greater than the wavelength maximum of the excitation spectrum of the donor fluorescent moiety. Accordingly, efficient non-radiative energy transfer can be produced therebetween.

Fluorescent donor and corresponding acceptor moieties are generally chosen for (a) high efficiency Forster energy transfer; (b) a large final Stokes shift (>100 nm); (c) shift of the emission as far as possible into the red portion of the visible spectrum (>600 nm); and (d) shift of the emission to a higher wavelength than the Raman water fluorescent emission produced by excitation at the donor excitation wavelength. For example, a donor fluorescent moiety can be chosen that has its excitation maximum near a laser line (for example, Helium-Cadmium 442 nm or Argon 488 nm), a high extinction coefficient, a high quantum yield, and a good overlap of its fluorescent emission with the excitation spectrum of the corresponding acceptor fluorescent moiety. A corresponding acceptor fluorescent moiety can be chosen that has a high extinction coefficient, a high quantum yield, a good overlap of its excitation with the emission of the donor fluorescent moiety, and emission in the red part of the visible spectrum (>600 nm).

Representative donor fluorescent moieties that can be used with various acceptor fluorescent moieties in FRET technology include fluorescein, Lucifer Yellow, B-phycoerythrin, 9-acridineisothiocyanate, Lucifer Yellow VS, 4-acetamido-4'-isothiocyanatostilbene-2,2'-disulfonic acid, 7-diethylamino-3-(4'-isothiocyanatophenyl)-4-methylcoumarin, succinimdyl 1-pyrenebutyrate, and 4-acetamido-4'-isothiocyanatostilbene-2,2'-disulfonic acid derivatives. Representative acceptor fluorescent moieties, depending upon the donor fluorescent moiety used, include LC Red 640, LC Red 705, Cy5, Cy5.5, Lissamine rhodamine B sulfonyl chloride, tetramethyl rhodamine isothiocyanate, rhodamine×isothiocyanate, erythrosine isothiocyanate, fluorescein, diethylenetriamine pentaacetate, or other chelates of Lanthanide ions (e.g., Europium, or Terbium). Donor and acceptor fluorescent moieties can be obtained, for example, from Molecular Probes (Junction City, Oreg.) or Sigma Chemical Co. (St. Louis, Mo.).

The donor and acceptor fluorescent moieties can be attached to the appropriate probe oligonucleotide via a linker arm. The length of each linker arm is important, as the linker arms will affect the distance between the donor and acceptor fluorescent moieties. The length of a linker arm for the purpose of the present invention is the distance in Angstroms (Å) from the nucleotide base to the fluorescent moiety. In general, a linker arm is from about 10 Å to about 25 Å. The linker arm may be of the kind described in WO 84/03285. WO 84/03285 also discloses methods for attaching linker arms to a particular nucleotide base, and also for attaching fluorescent moieties to a linker arm.

An acceptor fluorescent moiety such as an LC Red 640-NHS-ester can be combined with C6-Phosphoramidites (available from ABI (Foster City, Calif.) or Glen Research (Sterling, Va.)) to produce, for example, LC Red 640-Phosphoramidite. Frequently used linkers to couple a donor fluorescent moiety such as fluorescein to an oligonucleotide include thiourea linkers (FITC-derived, for example, fluorescein-CPG's from Glen Research or ChemGene (Ashland, Mass.)), amide-linkers (fluorescein-NHS-ester-derived, such as fluorescein-CPG from BioGenex (San Ramon, Calif.)), or 3'-amino-CPGs that require coupling of a fluorescein-NHS-ester after oligonucleotide synthesis.

Detection of a SNP in a Target Nucleic Acid in a Sample

The present disclosure provides methods for detecting the presence or absence of a SNP in a target nucleic acid in a biological or non-biological sample. Methods provided by the invention avoid problems of sample contamination, false negatives, and false positives. The methods include performing at least one cycling step that includes amplifying a portion of the target nucleic acid molecule from a sample using one or a pairs of primers, a hybridization step including contacting the amplification product with a melting probe, and a detecting step. Multiple cycling steps are performed, preferably in a thermocycler. The disclosed methods can be performed using the wild type or SNP specific probes, depending of the design chosen, to detect the presence of or absence of the SNP in the target nucleic acid in the sample.

As described herein, amplification products can be detected using labeled melting probes that take advantage of FRET technology. One FRET format utilizes one single-stranded melting probe labeled with two fluorescent moieties. When a first fluorescent moiety is excited with light of a suitable wavelength, the absorbed energy is transferred to a second fluorescent moiety according to the principles of FRET. The second fluorescent moiety is generally a quencher molecule. During the annealing step of the PCR reaction, the labeled melting probe binds to the target DNA (i.e., the amplification product) and as a result, the excited fluorescent moiety and the quencher moiety become spatially separated from one another. As a consequence, upon excitation of the first fluorescent moiety in the absence of the quencher, the fluorescence emission from the first fluorescent moiety can be detected.

Molecular beacons in conjunction with FRET can also be used to detect the presence of an amplification product using the real-time PCR methods of the invention. Molecular beacon technology uses a hybridization probe labeled with a first fluorescent moiety and a second fluorescent moiety. The second fluorescent moiety is generally a quencher, and the fluorescent labels are typically located at each end of the probe. Molecular beacon technology uses a probe oligonucleotide having sequences that permit secondary structure formation (e.g., a hairpin). As a result of secondary structure formation within the probe, both fluorescent moieties are in spatial proximity when the probe is in solution. After hybridization to the target nucleic acids (i.e., amplification products), the secondary structure of the probe is disrupted and the fluorescent moieties become separated from one another such that after excitation with light of a suitable wavelength, the emission of the first fluorescent moiety can be detected.

Depending on the design of the assay, the presence of FRET can indicate the presence of the target nucleic acid in the sample, and the absence of FRET can indicate the absence of the target nucleic acid in the sample. For example, decreasing shift in the predefined melting temperature of the hybridization probes is indicative of the presence of the SNP in the sample and wherein the absence of a decreasing shift in the predefined melting temperature of the hybridization probe is indicative of the absence of the SNP in the sample.

Representative biological samples that can be used include, but are not limited to dermal swabs, nasal swabs, wound swabs, blood cultures, skin, and soft tissue infections. Collection and storage methods of biological samples are known to those of skill in the art. Biological samples can be processed (e.g., by nucleic acid extraction methods and/or kits known in the art) to release the nucleic acid or in some cases, the biological sample can be contacted directly with the PCR reaction components and the appropriate oligonucleotides.

Melting curve analysis is a step that can be included in a cycling profile. Melting curve analysis is based on the fact that DNA melts at a characteristic temperature called the melting temperature (Tm), which is defined as the temperature at which half of the DNA duplexes have separated into single strands. The melting temperature of a DNA depends primarily upon its nucleotide composition. Thus, DNA molecules rich in G and C nucleotides have a higher Tm than those having an abundance of A and T nucleotides. By detecting the temperature at which signal is lost, the melting temperature of probes can be determined. Similarly, by detecting the temperature at which signal is generated, the annealing temperature of probes can be determined. Depending on the design of an assay, the actual predetermined melting temperature of the melting probe from the amplification products (in the case of using a melting probe having s SNP specific sequence), or a decreasing shift from the predetermined melting temperatures (in the case of using a melting probe having s wild type sequence) can confirm the presence or absence of the SNP in the target nucleic acid sequence in the sample.

Within each thermocycler run, control samples can be cycled as well. Positive control samples can amplify a nucleic acid control template (other than described amplification products of target nucleic acid sequence) using, for example, control primers and control probes. Positive control samples can also amplify, for example, a plasmid construct containing a nucleic acid molecules. Such a plasmid control can be amplified internally (e.g., within the sample) or in a separate sample run side-by-side with the patient's sample. Each thermocycler run can also include a negative control that, for example, lacks the target template DNA. Such controls are indicators of the success or failure of the amplification, hybridization, and/or FRET reaction. Therefore, control reactions can readily determine, for example, the ability of primers to anneal with sequence-specificity and to initiate elongation, as well as the ability of probes to hybridize with sequence-specificity and for FRET to occur.

In an embodiment, the methods of the invention include steps to avoid contamination. For example, an enzymatic method utilizing uracil-DNA glycosylase is described in U.S. Pat. Nos. 5,035,996, 5,683,896 and 5,945,313 to reduce or eliminate contamination between one thermocycler run and the next.

Conventional PCR methods in conjunction with FRET technology can be used to practice the described methods. In one embodiment, a LightCycler® instrument is used. The following patent applications describe real-time PCR as used in the LightCycler® technology: WO 97/46707, WO 97/46714, and WO 97/46712.

It is understood that the embodiments of the present invention are not limited by the configuration of one or more commercially available instruments.

Articles of Manufacture/Kits

Embodiments of the present invention further provides for articles of manufacture or kits to detect a SNP in a target nucleic acid in a sample. An article of manufacture can include primers and melting probes used to detect the SNP in the target nucleic acid, together with suitable packaging materials. Representative primers and melting probes for detection of SNP in a target nucleic acid in a sample are capable of hybridizing to the target nucleic acid molecules. In addition, the kits may also include suitably packaged reagents and materials needed for DNA immobilization, hybridization, and detection, such solid supports, buffers, enzymes, and DNA standards. Methods of designing primers and melting probes are disclosed herein, and representative examples of primers and melting probes that amplify and hybridize to the target nucleic acid molecules are provided.

Articles of manufacture of the invention can also include one or more fluorescent moieties for labeling the melting probes or, alternatively, the melting probes supplied with the kit can be labeled. For example, an article of manufacture may include a donor and/or an acceptor fluorescent moiety for labeling the melting probes. Examples of suitable FRET donor fluorescent moieties and corresponding acceptor fluorescent moieties are provided above.

Articles of manufacture can also contain a package insert or package label having instructions thereon for using the primers and melting probes to detect the presence or absence of SNP(s) in a target nucleic acid in a sample. Articles of manufacture may additionally include reagents for carrying out the methods disclosed herein (e.g., buffers, polymerase enzymes, co-factors, or agents to prevent contamination). Such reagents may be specific for one of the commercially available instruments described herein.

Embodiments of the disclosures will be further described in the following examples, which do not limit the scope of the invention described in the claims.

EXAMPLES

The following examples and figures are provided to aid the understanding of the present invention, the true scope of which is set forth in the appended claims. It is understood that modifications can be made in the procedures set forth without departing from the spirit of the invention.

Example I

Traditional Probe Melt Method

Figure 5:
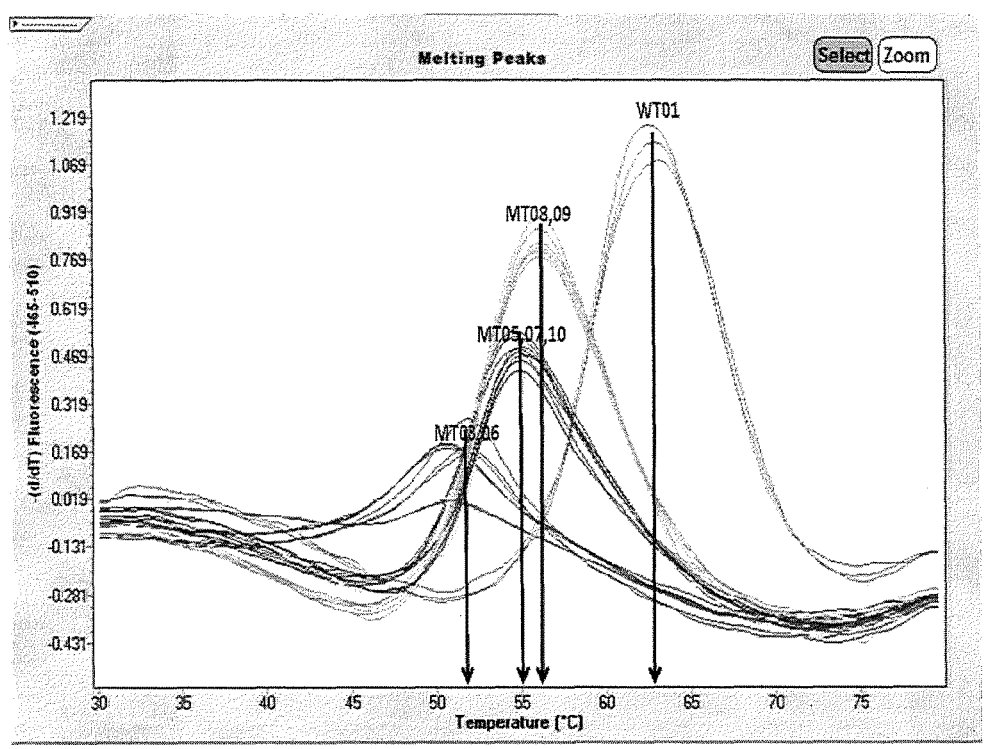
FIG. 5 shows a traditional melt curves analysis.

Referring to FIG. 5 and Table I, plasmid DNA (SEQ ID NOs: 2-9) were amplified using asymmetric PCR and immediately followed by melting analysis in a closed tube system. Asymmetric PCR contained an abundance of forward primer, limited reverse primer, and excess probe. The primers and probe design in this traditional probe melt method were designed not to overlap. The probe (SEQ ID NO: 1) was labeled at the 5'end with a fluorophore (F), and the 3'terminus with a black hole quencher (Q) which serves to quench the fluorescence of unbound probe and also to prevent amplification from probe extension.

TABLE I

Targets and Probe for Traditional Probe Melt Method

| SEQ ID NO | | SEQUENCE |
|---|---|---|
| 1 | Probe (WT) | 5'- FTGTGGGTCAACCCCGAQ -3' |
| 2 | Plasmid WT01A | 5'- CGCTTGTGGGTCAACCCCGA -3' |
| 3 | Plasmid MT03A | 5'- CGCTTGT_C_GGTCAACCCCGA -3' |
| 4 | Plasmid MT05A | 5'- CGCTTG_C_GGGTCAACCCCGA -3' |
| 5 | Plasmid MT06A | 5'- CGCTTGT_A_GGTCAACCCCGA -3' |

TABLE I-continued

Targets and Probe for Traditional Probe Melt Method

| SEQ ID NO | | SEQUENCE |
|---|---|---|
| 6 | Plasmid MT07A | 5'- CGCTTG_A_GGGTCAACCCCGA -3' |
| 7 | Plasmid MT08A | 5'- CGCTTGTGGGTCAACCCC_TA_ -3' |
| 8 | Plasmid MT09A | 5'- CGCTTGTGGGTCAACCCC_AA_ -3' |
| 9 | Plasmid MT10A | 5'- CGCTTGTGGGTCAACCCC_C_A -3' |

PCR conditions: 50 uL total reaction volume containing 24 uL of elution buffer (Tris, Methylparaben, Sodium Azide), 1 µL of plasmid DNA (~1e4c/uL), plus 25 µL of master mix (Tricine, Potassium Acetate, Glycerol, DMSO, Tween 20, EDTA, Sodium Azide, dATP, dCTP, dGTP, dUTP, Polymerase, FWD primer, REV primer, probe).

Melting analysis (post PCR): 5 sec at 94° C. followed by 30-80° C., ramp rate 0.06° C./sec.

Traditional melt analysis: Highest melting temperature occurs from WT probe and perfectly matched WT target (WT01: ~63° C.). Lower $T_m$ is caused by any SNP occurring under probe region, including silent mutations (MT03A-MT10A). The amount of $T_m$ shift is indicative of severity and location of a particular SNP under the probe region.

Example II

Overlapping Primer and Probe Melt Method with WT Probe

Figure 6:
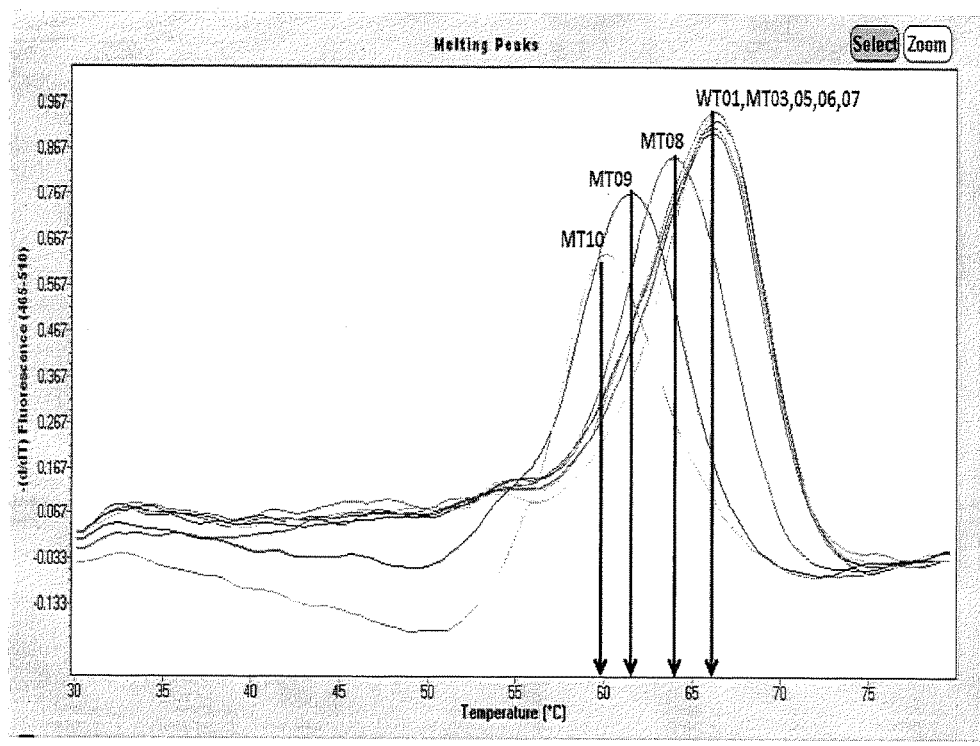
FIG. 6 shows a melt curve analysis utilizing the overlapping primer and probe design in an embodiment wherein the probe includes the wild type sequence.

Referring to FIG. 6 and Table II, plasmid DNA (SEQ ID NOs: 12-19) was amplified using asymmetric PCR and immediately followed by melting analysis in a closed tube system. Asymmetric PCR contained an abundance of forward primer, limited reverse primer, and excess probe. The probe (SEQ ID NO: 11) was designed to overlap the reverse primer (SEQ ID NO: 10) and was designed in the same sense as the reverse primer in order to avoid probe-primer interaction. The probe was labeled at the 5'end with a fluorophore, and the 3'terminus with a black hole quencher which serves to quench the fluorescence of unbound probe and also to prevent amplification from probe extension.

TABLE II

Targets and Stacked Primer and WT Probe

| SEQ ID NO | | SEQUENCE |
|---|---|---|
| 10 | Primer(WT) | 5'- GCGCTTGTGGGTCAACCCC -3' |
| 11 | Probe(WT) | 5'- FCGCTTGTGGGTCAACCCC_G_Q -3' |
| 12 | Plasmid WT01 | 5'- CGCTTGTGGGTCAACCCCG -3' |
| 13 | Plasmid MT03 | 5'- CGCTTGT_C_GGTCAACCCCG -3' |
| 14 | Plasmid MT05 | 5'- CGCTTG_C_GGGTCAACCCCG -3' |
| 15 | Plasmid MT06 | 5'- CGCTTGT_A_GGTCAACCCCG -3' |
| 16 | Plasmid MT07 | 5'- CGCTTG_A_GGGTCAACCCCG -3' |

TABLE II-continued

Targets and Stacked Primer and WT Probe

| SEQ ID NO | | SEQUENCE |
|---|---|---|
| 17 | Plasmid MT08 | 5'- CGCTTGTGGGTCAACCCCT -3' |
| 18 | Plasmid MT09 | 5'- CGCTTGTGGGTCAACCCCA -3' |
| 19 | Plasmid MT10 | 5'- CGCTTGTGGGTCAACCCCC -3' |

PCR conditions: 50 uL total reaction volume containing 24 uL of elution buffer (Tris, Methylparaben, Sodium Azide), 1 µL of plasmid DNA (~1e4c/uL), plus 25 µL of master mix (Tricine, Potassium Acetate, Glycerol, DMSO, Tween 20, EDTA, Sodium Azide, dATP, dCTP, dGTP, dUTP, Polymerase, FWD primer, REV primer, probe).

Melting analysis (post PCR): 5 sec at 94° C. followed by 30-80° C., ramp rate 0.06° C./sec.

Positive detection of three SNP's at 3' probe terminus: Melting analysis with stacked primer and probe indicating equivalent $T_m$ (~66° C.) from WT target (WT01) and silent mutations under probe region (MT03, 05, 06, and 07). $T_m$ shift only occurs from SNP's located at 3' probe terminus (MT08, MT09, and MT10), and amount of $T_m$ shift is specific to base pair change (MT08 Tm: ~64° C., MT09: ~61° C., MT10: ~59° C.).

Example III

Overlapping Primer and Probe Melt Method with SNP Specific Probe

Figure 7:
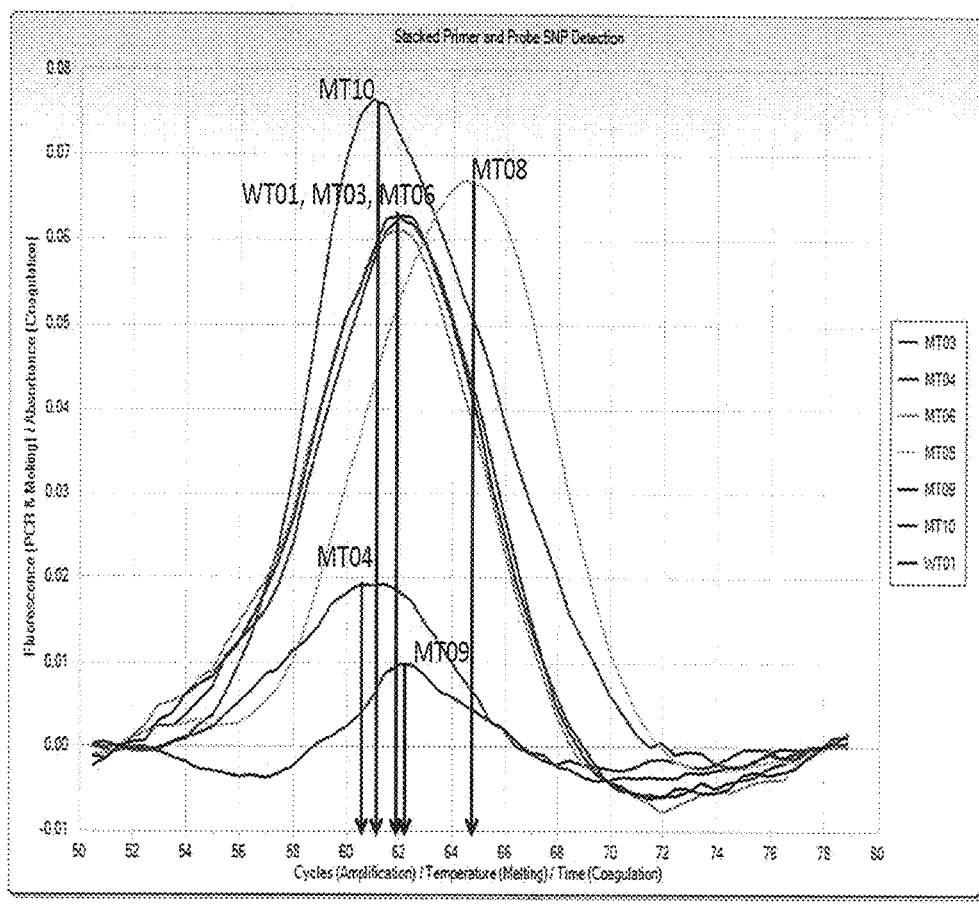
FIG. 7 shows a melt curve analysis utilizing the overlapping primer and probe design in an embodiment wherein the probe includes the SNP specific sequence.

Referring to FIG. 7 and Table III, plasmid DNA (SEQ ID NO: 12-19) was amplified using asymmetric PCR and immediately followed by melting analysis in a closed tube system. Asymmetric PCR contained an abundance of forward primer, limited reverse primer, and excess probe. The probe (SEQ ID NO: 20) was designed to overlap the reverse primer (SEQ ID NO: 10) and was designed in the same sense as the reverse primer in order to avoid probe-primer interaction. The probe was labeled at the 5'end with a fluorophore, and the 3'terminus with a black hole quencher which serves to quench the fluorescence of unbound probe and also to prevent amplification from probe extension.

TABLE III

Targets and Stacked Primer and SNP Specific Probe

| SEQ ID NO | | SEQUENCE |
|---|---|---|
| 10 | Primer (WT) | 5'- GCGCITGTGGGTCAACCCC -3' |
| 20 | Probe (SNP) | 5'- FCGCTTGTGGGTCAACCCCTQ -3' |
| 12 | Plasmid WT01A | 5'- CGCTTGTGGGTCAACCCCG -3' |
| 13 | Plasmid MT03A | 5'- CGCTTGTCGGTCAACCCCG -3' |
| 14 | Plasmid MT05A | 5'- CGCTTGCCGGTCAACCCCG -3' |
| 15 | Plasmid MT06A | 5'- CGCTTGTAGGTCAACCCCG -3' |
| 16 | Plasmid MT07A | 5'- CGCTTGAGGGTCAACCCCG -3' |
| 17 | Plasmid MT08A | 5'- CGCTTGTGGGTCAACCCCT -3' |
| 18 | Plasmid MT09A | 5'- CGCTTGTGGGTCAACCCCA -3' |
| 19 | Plasmid MT10A | 5'- CGCTTGTGGGTCAACCCCC -3' |

PCR conditions: 50 uL total reaction volume containing 24 uL of elution buffer (Tris, Methylparaben, Sodium Azide), 1 µL of plasmid DNA (~1e4c/uL), plus 25 µL of master mix (Tricine, Potassium Acetate, Glycerol, DMSO, Tween 20, EDTA, Sodium Azide, dATP, dCTP, dGTP, dUTP, Polymerase, FWD primer, REV primer, probe).

Melting analysis (post PCR): 5 sec at 94° C. followed by 30-80° C., ramp rate 0.06° C./sec.

Positive detection of one SNP at 3' probe terminus: Melting analysis with stacked primer and probe indicating highest $T_m$ (~65° C.) from MT08 probe only with matching MT08 target. All other mutations under probe region (indicated by targets MT03, 05, 06, and 07, MT09, and MT10) cause shifted $T_m$ (~60-62° C.).

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed:

1. A method for detecting a single nucleotide polymorphism (SNP) of interest in a target nucleic acid in a sample, the method comprising:

performing an amplifying step comprising contacting the sample with a primer comprising a first wild type nucleic acid sequence to produce an amplification product if any target nucleic acid is present in the sample;

performing a hybridizing step comprising contacting the amplification product with a melting probe comprising a second wild type nucleic acid sequence comprising a predefined melting temperature, wherein the second wild type nucleic acid sequence of the melting probe is the same as the first wild type nucleic acid sequence of the primer except it extends out at one end by exactly one nucleotide over where the SNP of interest is located; and detecting the presence or absence of the SNP of interest in the amplification product, wherein a decreasing shift in the predefined melting temperature of the melting probe is indicative of the presence of the SNP of interest in the sample and wherein the absence of a decreasing shift in the predefined melting temperature of the melting probe is indicative of the absence of the SNP of interest in the sample, wherein the target nucleic acid comprises a non-conserved region with one or more mutations different from the SNP of interest located where the primer hybridizes to the target nucleic acid.

2. The method of claim 1, wherein the melting probe is labeled with a fluorescent moiety at the 5' terminus, and a corresponding acceptor moiety at the 3' terminus to quench the fluorescence of unbound melting probes.

3. A method for detecting a single nucleotide polymorphism (SNP) of interest in a target nucleic acid in a sample, the method comprising:

performing an amplifying step comprising contacting the sample with a primer comprising a wild type nucleic acid sequence to produce an amplification product if any target nucleic acid is present in the sample;

performing a hybridizing step comprising contacting the amplification product with a melting probe comprising a nucleic acid sequence specific for the SNP of interest comprising a predefined melting temperature, wherein the nucleic acid sequence of the melting probe is the same as the wild type nucleic acid sequence of the primer except it extends out at one end by exactly one nucleotide over where the SNP of interest is located; and detecting the presence or absence of the SNP of interest in the amplification product, wherein a decreasing shift in the predefined melting temperature of the melting probe is indicative of the absence of the SNP of interest in the sample and wherein the absence of a decreasing shift in the predefined melting temperature of the melting probe is indicative of the presence of the SNP of interest in the sample, wherein the target nucleic acid comprises a non-conserved region with one or more mutations different from the SNP of interest located where the primer hybridizes to the target nucleic acid.

4. The method of claim 3, wherein the melting probe is labeled with a fluorescent moiety at the 5' terminus, and a corresponding acceptor moiety at the 3' terminus to quench the fluorescence of unbound melting probes.

5. A kit comprising a primer and probe set for detecting a single nucleotide polymorphism (SNP) of interest in a target nucleic acid in a sample, comprising:

a primer comprising a first wild type nucleic acid sequence to produce an amplification product if any target nucleic acid is present in the sample; and a melting probe comprising a second wild type nucleic acid sequence comprising a predefined melting temperature, wherein the second wild type nucleic acid sequence of the melting probe is the same as the first wild type nucleic acid sequence of the primer except it extends out at one end by exactly one nucleotide over where the SNP of interest is located;

wherein the presence or absence of the SNP of interest in the amplification product is detected whereby a decreasing shift in the predefined melting temperature of the melting probe is indicative of the presence of the SNP of interest in the sample and whereby the absence of a decreasing shift in the predefined melting temperature of the melting probe is indicative of the absence of the SNP of interest in the sample, wherein the target nucleic acid comprises a non-conserved region with one or more mutations different from the SNP of interest located where the primer hybridizes to the target nucleic acid, wherein the melting probe is labeled with a fluorescent moiety, and a corresponding acceptor moiety to quench the fluorescence of unbound melting probes.

6. The kit of claim 5, wherein the melting probe is labeled with a fluorescent moiety at the 5' terminus, and a corresponding acceptor moiety at the 3' terminus to quench the fluorescence of unbound melting probes.

7. The method of claim 1, wherein the primer consists of SEQ ID NO: 10 and the melting probe consists of SEQ ID NO: 11.

8. The method of claim 3, wherein the primer consists of SEQ ID NO: 10 and the melting probe consists of SEQ ID NO: 20.

9. The kit of claim 5, wherein the primer consists of SEQ ID NO: 10 and the melting probe consists of SEQ ID NO: 11.

* * * * *